US007515679B2

(12) United States Patent
Tacconi et al.

(10) Patent No.: US 7,515,679 B2
(45) Date of Patent: Apr. 7, 2009

(54) METHOD AND SYSTEM FOR CONE BEAM X-RAY SOURCE AND DETECTOR ARRANGEMENT IN COMPUTED TOMOGRAPHY SYSTEMS

(75) Inventors: Attilio Tacconi, Verona (IT); Pierluigi Mozzo, Verona (IT)

(73) Assignee: QR (Quantitative Radiography) SRL, Verona (IT)

( * ) Notice: Subject to any disclaimer, the term of this patent is extended or adjusted under 35 U.S.C. 154(b) by 14 days.

(21) Appl. No.: 11/809,630

(22) Filed: Jun. 1, 2007

(65) Prior Publication Data

US 2008/0298554 A1 Dec. 4, 2008

(51) Int. Cl.
*G01N 23/00* (2006.01)
(52) U.S. Cl. .......................................... 378/17; 378/15
(58) Field of Classification Search .............. 378/4–20, 378/38–39, 196–197
See application file for complete search history.

(56) References Cited

U.S. PATENT DOCUMENTS 4,039,837 A * 8/1977 Ohta et al. ..................... 378/39
7,197,107 B2 * 3/2007 Arai et al. ...................... 378/20

* cited by examiner

*Primary Examiner*—Hoon Song
(74) *Attorney, Agent, or Firm*—Cooper & Dunham LLP

(57) ABSTRACT

Methods and systems for x-ray detector and x-ray source arrangement in cone beam computed tomography systems are provided. An arm having a first end and a second end is mounted onto a support structure such that the arm rotates about a vertical axis. An x-ray source and an x-ray detector are separately attached to each end of the arm at angles in a range of about 2 to 20 degrees from the vertical axis, such that each is adapted to rotate with the arm about the vertical axis. The x-ray source and the x-ray detector are spaced apart to enable an anatomical target to be interposed between the x-ray source and the x-ray detector for cone beam computed tomography scanning, such that the x-ray source and the x-ray detector do not interfere with the target during scanning.

10 Claims, 5 Drawing Sheets

| | |
|---|---|
| Mount an arm having a first end and a second end onto a support structure such that the arm rotates about a vertical axis. | S401 |
| Attach an x-ray source to the first end of the arm at an angle in a range of about 2 to 20 degrees from the vertical axis such that the x-ray source rotates with the arm about the vertical axis. | S402 |
| Attach an x-ray detector to the second end of the arm at an angle in a range of about 2 to 20 degrees from the vertical axis such that the x-ray detector rotates with the arm about the vertical axis | S403 |
| Space the x-ray source and the x-ray detector apart to enable an anatomical target to be interposed between the x-ray source and the x-ray detector for cone beam computed tomography scanning, such that the x-ray source and the x-ray detector do not interfere with the subject during scanning. | S404 |

FIGURE 5

| | |
|---|---|
| Mount an arm having a first end and a second end onto a support structure such that the arm rotates about a vertical axis. | S501 |
| Attach an x-ray source to the first end of the arm parallel to the vertical axis such that the x-ray source rotates with the arm about the vertical axis | S502 |
| Attach an x-ray detector to the second end of the arm at an angle in a range of about 2 to 20 degrees from the vertical axis such that the x-ray detector rotates with the arm about the vertical axis | S503 |
| Space the x-ray source and the x-ray detector apart to enable an anatomical target to be interposed between the x-ray source and the x-ray detector for cone beam computed tomography scanning, such that the x-ray source and the x-ray detector do not interfere with the subject during scanning. | S504 |

METHOD AND SYSTEM FOR CONE BEAM X-RAY SOURCE AND DETECTOR ARRANGEMENT IN COMPUTED TOMOGRAPHY SYSTEMS

BACKGROUND

1. Field of the Invention

The present disclosure relates generally to cone beam computed tomography, and more particularly, to a method and system for cone beam x-ray source and detector arrangement in computed tomography systems.

2. Background of the Invention

Cone beam computed tomography ("CBCT") is utilized for obtaining tomographic radiographic images of the dentomaxillo facial region. By combining CBCT with x-ray detection units, tomographic radiographic images of the dentomaxillo facial region are obtained by acquiring a sequence of two-dimensional radiographic images during rotation of an arm around the anatomical part of interest. The existing systems can be implemented for both a standing patient, as illustrated in FIG. 1A, and a sitting patient, as illustrated in FIG. 1B. For example, existing cone beam 14 systems include an arm 10, an arm support structure 11, an x-ray source 12, an x-ray image detector 13, electric motors to actuate rotational movements and vertical transitional movements, motor control electronic circuitry, electronic circuitry to control and drive the x-ray source 12 and x-ray image detector 13, and a computer for controlling the electronic circuitry, and processing and displaying acquired data and images. The arm 10 is translatable along the vertical axis to adjust, for example, to the patient's height, and can be vertically rotated 360 degrees around a rotational axis which corresponds to the anatomical target.

Both the x-ray source 12 and x-ray image detector 13 are rigidly connected on opposite ends of the arm 10, and are arranged to rotate about a vertical axis. However, with this arrangement, both the x-ray source 12 and the x-ray image detector 13 must be sufficiently far from the anatomical part of interest, for example, a patient's head, so as not to interfere with the patient during rotation, for example, the patient's shoulder. For example, FIG. 1A shows that if the arm 10 were to rotate about a vertical axis, there is a high likelihood that the x-ray image detector 13 would contact the patient's shoulder. The gap d between the detector and the patient's shoulder is very tight. But, if the x-ray image detector 13 is moved further away from the source 12 so as not to contact the patient's shoulder during operation, it would affect image acquisition by drastically reducing the field of view of the system.

Accordingly, there is a need for an improved x-ray detector and x-ray source arrangement that retains a wide field of view for radiographic image acquisition, so that while a cone beam computed tomography system is operating, the x-ray detector and x-ray source do not come into contact with the patient.

SUMMARY OF THE INVENTION

To that end, the present invention contemplates improved CBCT systems and methods for arranging the components in a CBCT system. A cone beam computed tomography system includes, a support structure comprising an arm having a first end and a second end, wherein the arm is mounted to rotate about a vertical axis, an x-ray source is attached to the first end of the arm at an angle in a range of about 2 to 20 degrees from the vertical axis and adapted to rotate therewith about the vertical axis, and an x-ray detector is attached to the second end of the arm at an angle in a range of about 2 to 20 degrees from the vertical axis and adapted to rotate therewith about the vertical axis, wherein the x-ray source and the x-ray detector are spaced apart to enable an anatomical target to be interposed between the x-ray source and the x-ray detector for cone beam computed tomography scanning, such that the x-ray source and the x-ray detector do not interfere with the subject during scanning.

Alternatively, a cone beam computed tomography system includes, a support structure comprising an arm having a first end and a second end, wherein the arm is mounted to rotate about a vertical axis, an x-ray source attached to the first end of the arm and adapted to rotate therewith about the vertical axis, an x-ray detector attached to the second end of the arm and adapted to rotate therewith about the vertical axis, wherein at least one of the x-ray source and the x-ray detector are attached to the arm at an angle in a range of about 2 to 20 degrees from the vertical axis, and wherein the x-ray source and the x-ray detector are spaced apart to enable an anatomical target to be interposed between the x-ray source and the x-ray detector for cone beam computed tomography scanning, such that the x-ray source and the x-ray detector do not interfere with the target during scanning.

In addition, the present invention also contemplates a cone beam computed tomography system includes a support structure comprising an arm having a first end and a second end, wherein the arm is mounted to rotate about a vertical axis, an x-ray source is attached to the first end of the arm parallel to the vertical axis and adapted to rotate therewith about the vertical axis, and an x-ray detector is attached to the second end of the arm at an angle in a range of about 2 to 20 degrees from the vertical axis and adapted to rotate therewith about the vertical axis, wherein the x-ray source and the x-ray detector are spaced apart to enable an anatomical target to be interposed between the x-ray source and the x-ray detector for cone beam computed tomography scanning, such that the x-ray source and the x-ray detector do not interfere with the subject during scanning.

The invention also contemplates a method for arranging the components in a CBCT system. The method includes, mounting an arm having a first end and a second end onto a support structure such that the arm rotates about a vertical axis, attaching an x-ray source to the first end of the arm at an angle in a range of about 2 to 20 degrees from the vertical axis such that the x-ray source rotates with the arm about the vertical axis, attaching an x-ray detector to the second end of the arm at an angle in a range of about 2 to 20 degrees from the vertical axis such that the x-ray detector rotates with the arm about the vertical axis, spacing the x-ray source and the x-ray detector apart to enable an anatomical target to be interposed between the x-ray source and the x-ray detector for cone beam computed tomography scanning, such that the x-ray source and the x-ray detector do not interfere with the subject during scanning.

Alternatively, a method for arranging components in a CBCT system includes, mounting an arm having a first end and a second end onto a support structure such that the arm rotates about a vertical axis, attaching an x-ray source to the first end of the arm such that the x-ray source rotates with the arm about the vertical axis, attaching an x-ray detector to the second end of the arm such that the x-ray detector rotates with the arm about the vertical axis, attaching at least one of the x-ray source and x-ray detector to the arm at an angle in a range of about 2 to 20 degrees from the vertical axis; and spacing the x-ray source and the x-ray detector apart to enable an anatomical target to be interposed between the x-ray source and the x-ray detector for cone beam computed tomography scanning, such that the x-ray source and the x-ray detector do not interfere with the target during scanning.

In addition, the present invention also contemplates a method for arranging the components in a CBCT system includes mounting an arm having a first end and a second end onto a support structure such that the arm rotates about a vertical axis, attaching an x-ray source to the first end of the arm parallel to the vertical axis such that the x-ray source rotates with the arm about the vertical axis, attaching an x-ray detector to the second end of the arm at an angle in a range of about 2 to 20 degrees from the vertical axis such that the x-ray detector rotates with the arm about the vertical axis, spacing the x-ray source and the x-ray detector apart to enable an anatomical target to be interposed between the x-ray source and the x-ray detector for cone beam computed tomography scanning, such that the x-ray source and the x-ray detector do not interfere with the subject during scanning.

BRIEF DESCRIPTION OF THE DRAWINGS

The features of the present application can be more readily understood from the following detailed description with reference to the accompanying drawings wherein:

FIG. 4 is a flow chart illustrating a method for arranging the components in a cone beam computed tomography system, according to one embodiment of the present invention; and FIG. 5 is a flow chart illustrating a method for arranging the components in a cone beam computed tomography system, according to another embodiment of the present invention.

DETAILED DESCRIPTION OF THE PREFERRED EMBODIMENTS

The present invention provides tools for an improved CBCT system and a method for arranging the components in a CBCT system so that the x-ray source and x-ray detector do not interfere with a patient during cone beam computed tomography scanning. The object of the present invention is to provide a CBCT system where either the x-ray detector or both the x-ray detector and the x-ray source are inclined with respect to the axis of rotation of the arm. This allows the x-ray detector and the x-ray source to rotate about a patient in order to perform a CBCT radiographic exam without coming in contact with the patient, while at the same time retaining a radiographic field of view as wide as practical.

Figure 1:
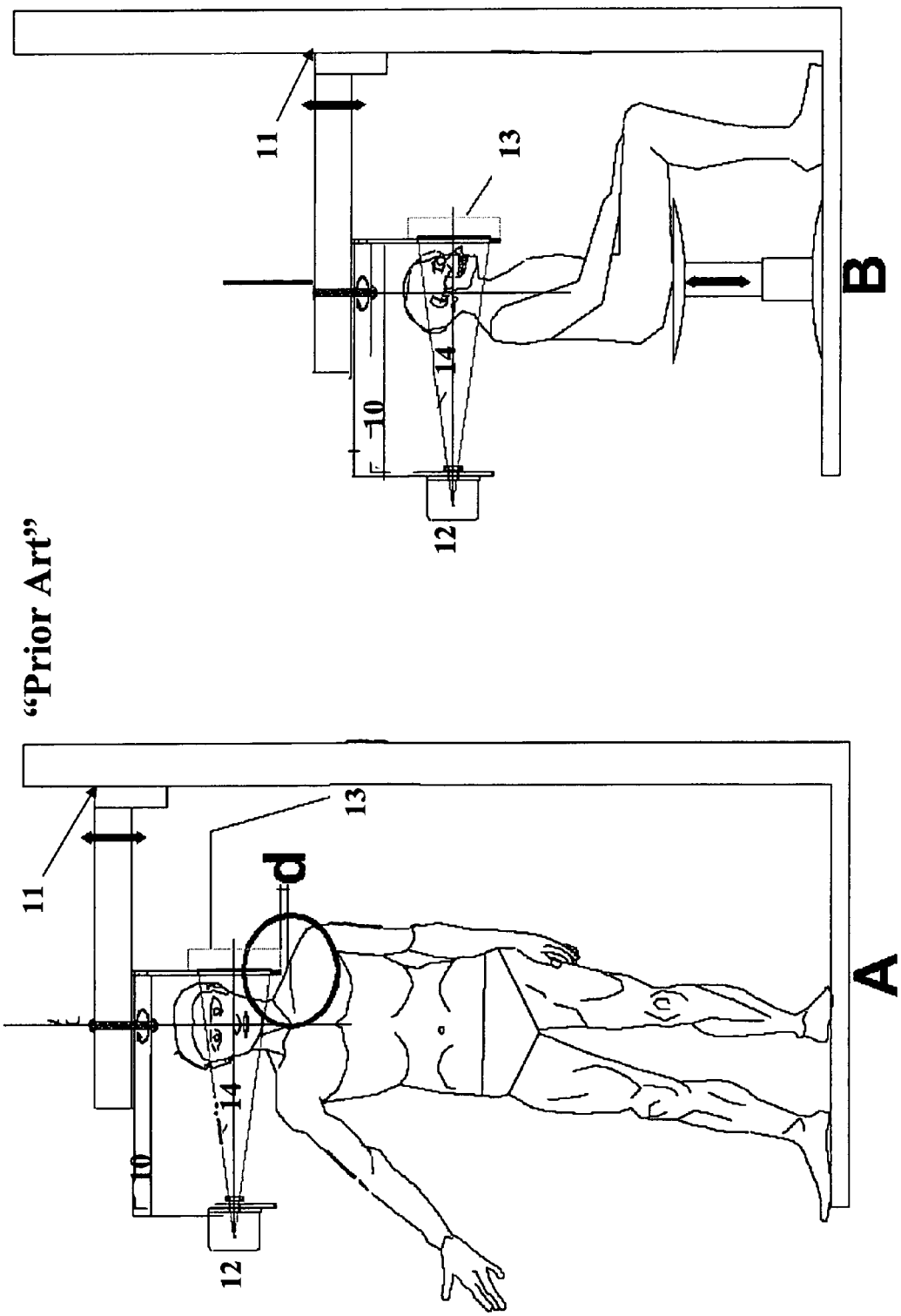
FIG. 1 is a diagram of a prior art cone beam computed tomography system.
Figure 2:
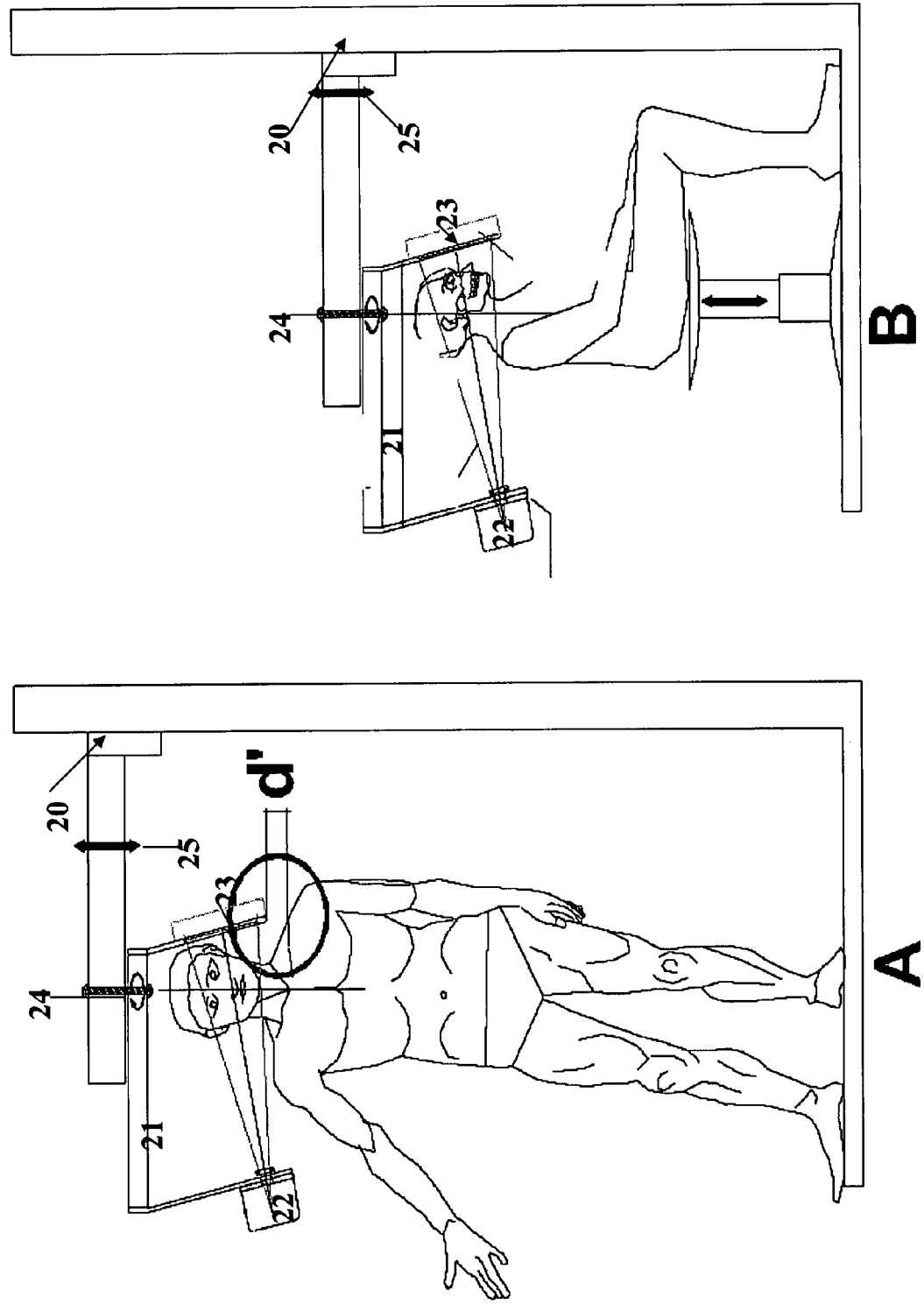
FIG. 2 is a diagram of a cone beam computed tomography system, according to one embodiment of the present invention.

FIG. 2 is a diagram showing an improved CBCT system, according to one embodiment of the present disclosure. The improved CBCT system can be implemented for both a standing patient, as illustrated in FIG. 2A, and a sitting patient, as illustrated in FIG. 2B. The CBCT system comprises a support structure 20, an arm 21, an x-ray source 22, and an x-ray detector 23. The arm 21 has a first end and a second end and is mounted to the support structure 20 to rotate about a vertical axis 24. According to an embodiment, the support structure 20 may include a seat for a patient to sit or a platform for a patient to stand and the arm is attached to the support structure so that it can be adjusted along the vertical axis 25 to accommodate a patient of any height. Alternatively, if a seat or platform is provided, the seat or platform may be adjusted along the vertical axis to accommodate the patient. An x-ray source 22 is attached to the first end of the arm at an angle in a range of about 2 to 20 degrees from the vertical axis and is adapted to rotate with the arm about the vertical axis. Similarly, an x-ray detector 23 may be attached to the second end of the arm at an angle in a range of about 2 to 20 degrees from the vertical axis and is also adapted to rotate with the arm about the vertical axis. According to a preferred embodiment, the x-ray detector 23 and/or the x-ray source 22 are attached to the arm at an angle of about 12.5 degrees from the vertical axis. While this embodiment is preferred, the 12.5 degree angle has been determined empirically and other angles may also be suitable.

Both the x-ray source 22 and the x-ray detector 23 are spaced apart to enable an anatomical target, for example, a patient's head, to be interposed therebetween for cone beam computed tomography scanning. In this configuration, when the arm 21 is rotated about the vertical axis 24, the x-ray source 22 and the x-ray detector 23 do not interfere with the target during scanning. For example, in FIG. 2, the gap represented by d' shows that the x-ray detector 23 will not touch the patient's shoulder while the arm 21 is rotating. In this configuration, the size of the field of view is increased.

Figure 3:
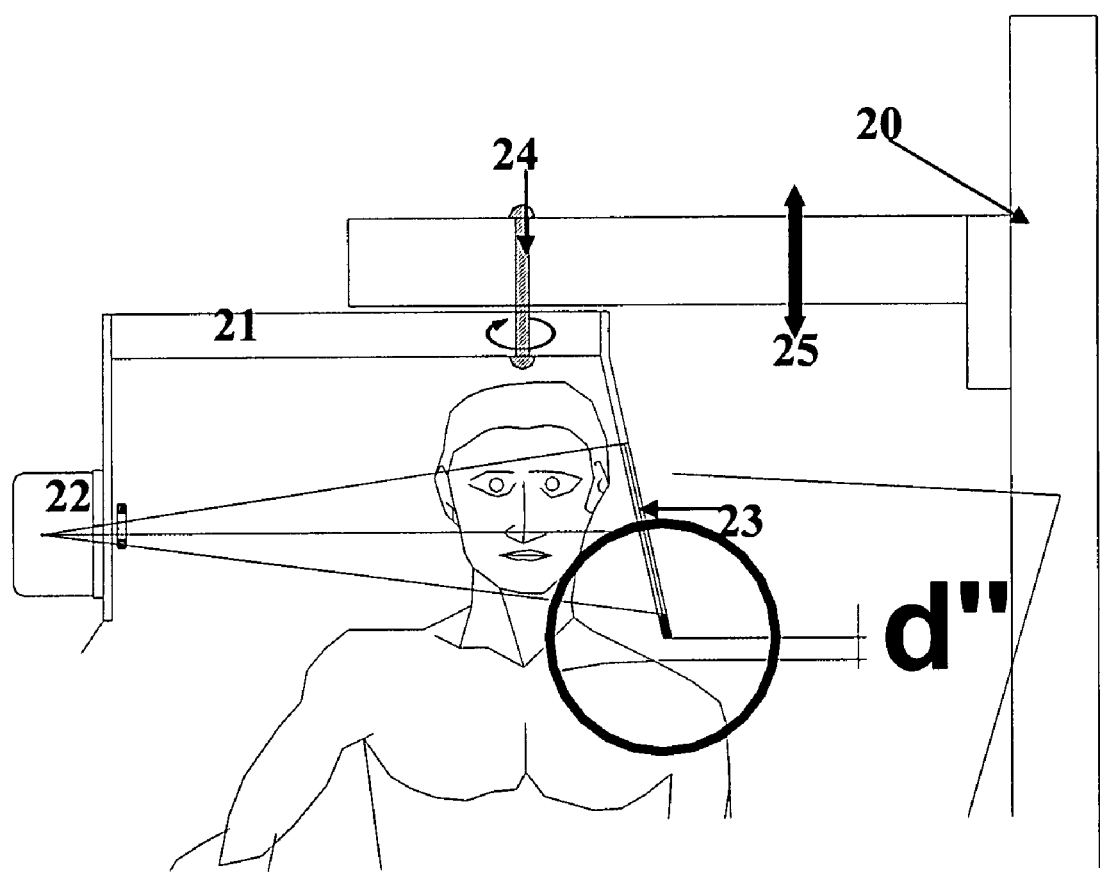
FIG. 3 is a diagram of a cone beam computed tomography system, according to another embodiment of the present invention.

FIG. 3 is a diagram showing an improved CBCT system, according to another embodiment of the present disclosure. Although not depicted, this configuration can be implemented for both a standing patient and a sitting patient. As is the case with the system illustrated in FIG. 2, this embodiment comprises a support structure 20, an arm 21, an x-ray source 22, and an x-ray detector 23. The arm 21 has a first end and a second end and is mounted to the support structure 20 to rotate about a vertical axis 24. An x-ray source 22 is attached to the first end of the arm parallel to the vertical axis and is adapted to rotate with the arm about the vertical axis. An x-ray detector 23 is attached to the second end of the arm at an angle in a range of about 2 to 20 degrees, for example, 12.5 degrees, from the vertical axis and is also adapted to rotate with the arm about the vertical axis. Both the x-ray source 22 and the x-ray detector 23 are spaced apart to enable an anatomical target, for example, a patient's head, to be interposed therebetween for cone beam computed tomography scanning. In this configuration, when the arm 21 is rotated about the vertical axis 24, the x-ray source 22 and the x-ray detector 23 do not interfere with the target during scanning. For example, in FIG. 2, the gap represented by d'' shows that the x-ray detector 23 will not touch the patient's shoulder while the arm 21 is rotating. In this configuration, the size of the field of view is also increased.

FIG. 4 is a flow chart illustrating a method for arranging the components in a cone beam computed tomography system, according to one embodiment of the present invention. An arm having a first end and a second end is mounted onto a support structure such that the arm rotates about a vertical axis (Step S401). According to an embodiment, the arm is mounted to the support structure so that it can be adjusted along the vertical axis. An x-ray source is attached to the first end of the arm at an angle in a range of about 2 to 20 degrees, for example, 12.5 degrees, from the vertical axis such that the x-ray source rotates with the arm about the vertical axis (Step S402). An x-ray detector attached to the second end of the arm at an angle in a range of about 2 to 20 degrees, for example, 12.5 degrees, from the vertical axis such that the x-ray detector rotates with the arm about the vertical axis (Step S403). The x-ray source and the x-ray detector are spaced apart to enable an anatomical target to be interposed therebetween for cone beam computed tomography scanning, such that the x-ray source and the x-ray detector do not interfere with the subject during scanning (Step S404).

FIG. 5 is a flow chart illustrating a method for arranging the components in a cone beam computed tomography system, according to another embodiment of the present invention. An arm having a first end and a second end is mounted onto a support structure such that the arm rotates about a vertical axis (Step S501). According to an embodiment, the arm is mounted to the support structure so that it can be adjusted along the vertical axis. An x-ray source is attached to the first end of the arm parallel to the vertical axis such that the x-ray source rotates with the arm about the vertical axis (Step S502). An x-ray detector attached to the second end of the arm at an angle in a range of about 2 to 20 degrees from the vertical axis such that the x-ray detector rotates with the arm about the vertical axis (Step S503). According to an embodiment, the x-ray detector is attached to the second end of the arm at an angle of about 12.5 degrees from the vertical axis. The x-ray source and the x-ray detector are spaced apart to enable an anatomical target to be interposed therebetween for cone beam computed tomography scanning, such that the x-ray source and the x-ray detector do not interfere with the target during scanning (Step S504).

It is also within the scope of the invention to incline the x-ray source at an angle of about 2 to 20 degrees, for example, 12.5 degrees, from the vertical axis while the x-ray detector is parallel to the vertical axis.

According to another embodiment, the angle of the x-ray source and/or x-ray detector can be predetermined and programmed into the system or it can be adjusted by the operator for each individual patient prior to CBCT scanning.

Numerous additional modifications and variations of the present invention are possible in view of the above teachings.

What is claimed is:

1. A cone beam computed tomography system, comprising:
   a support structure comprising an arm having a first end and a second end, wherein the arm is mounted to rotate about a vertical axis;
   an x-ray source attached to the first end of the arm at an angle in a range of about 2 to 20 degrees from the vertical axis and adapted to rotate therewith about the vertical axis;
   an x-ray detector attached to the second end of the arm at an angle in a range of about 2 to 20 degrees from the vertical axis and adapted to rotate therewith about the vertical axis;
   wherein the x-ray source and the x-ray detector are spaced apart to enable an anatomical target to be interposed between the x-ray source and the x-ray detector for cone beam computed tomography scanning, such that the x-ray source and the x-ray detector do not interfere with the target during scanning.

2. The system of claim 1, wherein the support structure comprises a platform for a patient to stand.

3. The system of claim 1, wherein the support structure comprises a seat or platform for a patient to sit.

4. The system of claim 1, wherein the arm is attached to the support structure so that it can be translated along the vertical axis to adjust for the height of the target.

5. The system of claim 1, wherein the x-ray source is attached to the first end of the arm at an angle of about 12.5 degrees from the vertical axis.

6. The system of claim 1, wherein the x-ray detector is attached to the second end of the arm at an angle of about 12.5 degrees from the vertical axis.

7. A method for arranging the components in a CBCT system, comprising:
   mounting an arm having a first end and a second end onto a support structure such that the arm rotates about a vertical axis;
   attaching an x-ray source to the first end of the arm at an angle in a range of about 2 to 20 degrees from the vertical axis such that the x-ray source rotates with the arm about the vertical axis;
   attaching an x-ray detector to the second end of the arm at an angle in a range of about 2 to 20 degrees from the vertical axis such that the x-ray detector rotates with the arm about the vertical axis;
   spacing the x-ray source and the x-ray detector apart to enable an anatomical target to be interposed between the x-ray source and the x-ray detector for cone beam computed tomography scanning, such that the x-ray source and the x-ray detector do not interfere with the target during scanning.

8. The method of claim 7, further comprising mounting the arm to the support structure so that it can be translated along the vertical axis to adjust for the height of the target.

9. The method of claim 7, wherein the x-ray source is attached to the first end of the arm at an angle of about 12.5 degrees from the vertical axis.

10. The method of claim 7, wherein the x-ray detector is attached to the second end of the arm at an angle of about 12.5 degrees from the vertical axis.

* * * * *